United States Patent [19]

Sebag et al.

[11] Patent Number: 4,787,911
[45] Date of Patent: Nov. 29, 1988

[54] SURFACE-ACTIVE OLIGOMERS, A PROCESS FOR THEIR PREPARATION AND COMPOSITIONS CONTAINING THEM

[75] Inventors: Henri Sebag, Paris; Guy Vanlerberghe, Claye-Souilly, both of France

[73] Assignee: L'Oreal, Paris, France

[21] Appl. No.: 942,718

[22] Filed: Dec. 17, 1986

Related U.S. Application Data

[62] Division of Ser. No. 557,212, Dec. 2, 1983, Pat. No. 4,656,030, which is a division of Ser. No. 285,422, Jul. 20, 1981, Pat. No. 4,430,250.

[30] Foreign Application Priority Data

Jul. 21, 1980 [LU] Luxembourg ............................ 82646

[51] Int. Cl.$^4$ .............................................. A61K 7/13
[52] U.S. Cl. ............................................. 8/405; 8/406
[58] Field of Search ................................... 8/406, 405

[56] References Cited

U.S. PATENT DOCUMENTS 4,656,030 4/1987 Sebag et al. ............................ 8/405
4,657,556 4/1987 Sebag et al. ............................ 8/405

Primary Examiner—Dale R. Ore
Attorney, Agent, or Firm—Cushman, Darby & Cushman

[57] ABSTRACT

The invention provides surface-active random oligomers of the general formula:

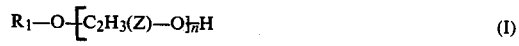

(I)

in which $R_1$ denotes a linear or branched, saturated or unsaturated aliphatic hydrocarbon radical or a cycloaliphatic, aromatic or alkylaromatic radical containing 1 to 30 carbon atoms, Z denotes a group A and/or at least one group corresponding to the formula (II)

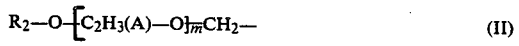

(II)

in which $R_2$ denotes a hydrocarbon radical having the meaning indicated for $R_1$ and containing a number of carbon atoms from 8 to 30, $\overline{n}$ denotes an average statistical value from 1 to 20, $\overline{m}$ denotes an average statistical value from 0.5 to 10 and A denotes a group of hydrophilic character. These oligomers can be used in cosmetic or pharmaceutical compositions.

6 Claims, No Drawings

SURFACE-ACTIVE OLIGOMERS, A PROCESS FOR THEIR PREPARATION AND COMPOSITIONS CONTAINING THEM

This is a division of application Ser. No. 557,212 filed Dec. 2, 1983 now U.S. Pat. No. 4,656,030 which is a division of application Ser. No. 285,422 filed July 20, 1981 now U.S. Pat. No. 4,430,250.

The present invention relates to surface-active oligomers, a process for their preparation and cosmetic or pharmaceutical compositions in which they are present.

A large number of surface-active agents consisting of a lipophilic aliphatic or arylaliphatic hydrocarbon fatty chain joined to a hydrophilic chain are already known. These products have found numerous applications in the most diverse fields.

It has already been proposed (see French Patent Application No. 2,359,165), to replce the single hydrocarbon chain of the conventional surface-active agents by a lipophilic sequence obtained by the polymerisation of an alkylene oxide or a glycidyl ether having a long chain.

More recently, other oligomers in which the distribution of the units of lipophilic character and of the units of hydrophilic character is random have been described. In fact, it has been found that these products possess improved properties compared with those described previously.

These oligomers are prepared using 1,2-epoxides as starting materials, these generally being expensive reactants which are not always available on an industrial scale and, in certain cases, are very difficult to prepare.

The alkyl glycidyl ethers also proposed as starting materials are even more expensive reactants. Moreover, these are compounds of high molecular weight, which cannot always be easily purified by distillation.

We have now discovered, according to the present invention, a new family of products which can be prepared using mixtures of compounds having an oxirane end group and generally containing more than one ether group, which mixtures are much easier to obtain industrially. As these starting materials do not need to be purified by distillation, they can be used direct from the reaction medium.

Apart from their very low industrial cost, these products exhibit the additional advantage that they can be prepared from any alcohol or mixture of alcohols of high molecular weight, and in particular from cuts of industrial fatty alcohols.

In the latter case, the corresponding mixtures of alkyl glycidyl ethers can not be purified by distillation without altering their compositions.

Despite the nature of the starting materials used, the products prepared in this way have a generally low aggressiveness towards the skin and the mucous membranes of the eye. They can thus be used as additives in cosmetic compositions or as excipients in pharmaceutic compositions.

Accordingly, the present invention provides new surface-active oligomers obtained by the random polyaddition, to an alcohol, of, essentially:

(1) a mixture of monoether and polyether compounds having an epoxide end group;
(2) an epihalogenohydrin and
(3) if appropriate, small proportions of a bis-epoxide or mixture of bis-epoxides, acting as a chain extender and/or crosslinking agent.

The invention also provides the process for the preparation of these compounds as well as cosmetic or pharmaceutical compositions based on these compounds.

The surface-active random oligomers according to the present invention are essentially represented by the following general formula (I):

$$R_1-O-[C_2H_3(Z)-O]_{\overline{n}}H \qquad (I)$$

in which $R_1$ denotes a linear or branched saturated or unsaturated aliphatic hydrocarbon radial or a cycloaliphatic, aromatic or alkylaromatic radical containing 1 to 30 carbon atoms, Z denotes a group A and/or at least once a group corresponding to the formula (II):

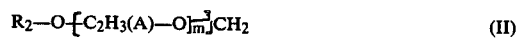

$$R_2-O-[C_2H_3(A)-O]_{\overline{m}}CH_2 \qquad (II)$$

in which $R_2$ denotes a hydrocarbon radical having the meaning indicated for $R_1$, containing a number of carbon atoms which can vary from 8 to 30, $\overline{n}$ denotes any average statistical value from 1 to 20, $\overline{m}$ denotes any average statistical value from 0.5 to 10 and preferably 0.5 to 5, and A denotes a group of hydrophilic character, which can, in general, be non-ionic, cationic, anionic or zwitterionic.

A can more particularly denote the following groups:

$$-CH_2OH \qquad (a)$$

$$\begin{array}{c} -S-CH_2-CH_2OH \text{ or} \\ \downarrow \\ (O)_u \end{array} \qquad (b)$$

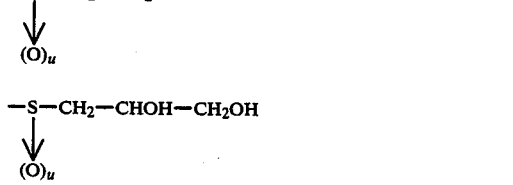

$$\begin{array}{c} -S-CH_2-CHOH-CH_2OH \\ \downarrow \\ (O)_u \end{array}$$

in which u denotes the value 0 or 1.

$$\begin{array}{c} \phantom{-}\diagup R_3 \\ -N \\ \phantom{-}\diagdown R_4 \\ \downarrow \\ (O)_u \end{array} \qquad (c)$$

in which $R_3$ and $R_4$, which are identical or different, denote alkyl or hydroxyalkyl radicals containing from 1 to 3 carbon atoms and more particularly methyl, ethyl and/or hydroxyethyl groups, or alternatively $R_3$ and $R_4$ form, with the nitrogen atom, a heterocyclic ring having 5 or 6 ring members and preferably a piperidino or morpholino group, and u denotes the value 0 or 1.

$$\begin{array}{c} \phantom{-}\diagup R_3 \\ -N \phantom{xx} .HV \\ \phantom{-}\diagdown R_4 \\ \downarrow \\ (O)_u \end{array} \qquad (d)$$

in which HV denotes a mineral or organic acid such as hydrochloric, hydrobromic, sulphuric, phosphoric, acetic, lactic, citric or tartaric acid u, $R_3$ and $R_4$ having the same meanings as those indicated for the group (c).

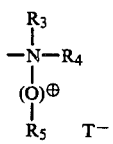 (e)

in which $R_5$ denotes a methyl, ethyl or hydroxyethyl radical, $T^{31}$ denotes an anion such as $Cl^-$, $Br^-$, $I^-$, $CH_3SO_3^-$, $CH_3SO_4^-$ or $CH_3-C_6H_4-SO_3^-$, u, $R_3$ and $R_4$ having the same meanings as those indicated for the group of the formula (c).

 (f)

in which $Q^-$ denotes a group $CH_2COO^-$, $CH_2-CH_2COO^-$ or $(CH_2)_3SO_3^-$, $R_3$ and $R_4$ having the same meanings as those indicated for the group (c).

$-OSO_3M$ (g)

in which M denotes a hydrogen atom or an alkali metal or on euivalent of an alkaline earth metal preferably sodium, potassium, ½ calcium or ½ magnesium.

$-OCOCH_2SO_3M$ (h)

in which M has the same meaning as that indicated for the group (g).

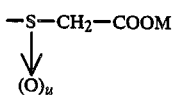 (i)

in which M has the same meaning as that indicated for the group (g) and u denotes 0 or 1, and also the crosslinked oligomers of the formula (I).

The groups $R_1$ and $R_2$ preferably denote linear or branched $C_6$ to $C_{20}$ alkyl or alkenyl radicals.

The mixture of compounds corresponding to the formula (I) according to the invention can be obtained from polyhalogenated compounds corresponding to the formula (III)

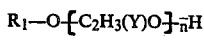 (III)

in which $R_1$ and $\overline{n}$ have the same meaning as that indicated above for the formula (I) and Y denotes the group $CH_2X$ and/or at least once the group of the formula (IV)

 (IV)

in which $R_2$ and $\overline{m}$ have the same meaning as that indicated for the formula (II). X denotes a halogen atom such as bromine or chlorine, and preferably a chlorine atom.

The intermediates of the formula (III) used for the preparation of the mixture of compounds according to the invention can be obtained by the polyaddition, to one molecule of a compound of the formulae $R_1OH$ (containing at least one hydroxyl group and serving as an initiator) of a mixture of $\overline{n}$ molecules of epoxides, consisting of:

(1) p molecules of products of the general formula (V), p being a number from 1 to 20:

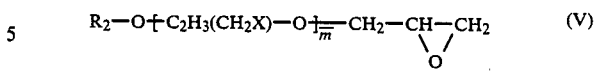 (V)

in which $R_2$, X and $\overline{m}$ have the same meaning as that indicated for the formula (IV), (2) (n-p) molecules of an epihalogenohydrin preferably epichlorohydrin, and, if appropriate, (3) q molecules of a diepoxide compound acting as a chain extender or crosslinking agent, q being from 0 to 0.05n.

The compounds corresponding to the formula $R_1OH$ which act as initiators or also telogens in the telomerisation reactions making it possible to prepare the compounds according to the invention are alcohols having from 1 to 30 carbon atoms, chosen from the aliphatic, cycloaliphatic or alkylaromatic series. Amongst these alcohols, saturated or unsaturated $C_6$ to $C_{20}$ alcohols may be mentioned in particular.

The epoxides corresponding to the formula (V) are products containing statistically more than one ether group in addition to the oxirene group and can themselves be obtained by the polyaddition of (m+1) molecules of an epihalogenohydrin, preferably epichlorohydrin, to one molecule of an alcohol of the formula $R_2OH$, in the presence of a Lewis acid catalyst such as $BF_3$, $SnCl_4$ or $SbCl_5$, at a temperature of, say, 20° to 100° C., followed by reaction with an alkaline agent such as sodium hydroxide or potassium hydroxide. The latter reaction, leading to cyclisation, is suitably carried out at 30° to 80° C., with or without a solvent. The solvents which can be used are preferably short-chain secondary or tertiary alcohols such as isopropyl or tert.-butyl alcohol. The resulting products are then washed with water and, if appropriate, neutralised with an acid, such as hydrochloric acid, in order to remove any trace of basicity, and dried by heating under reduced pressure.

The halogenated epoxides thus obtained can be used direct for the preparation of the intermediates corresponding to the formula (III). For this purpose, they are mixed with the epihalogenohydrin and, if appropriate, the diepoxide, and the mixture is then added progressively to the alcohol or to the mixture of alcohols corresponding to the formula $R_1OH$, in the presence of a Lewis acid catalyst, typically $BF_3$, $SnCl_4$ or $SbCl_5$, and, if appropriate, a solvent such as an aliphatic hydrocarbon, at a temperature of, say, 20° to 100° C., until the oxirane groups have completely reacted. When a diepoxide is used, this can also be introduced after the polyaddition reaction of the epihalogenohydrin and the compounds corresponding to the formula (V).

Diglycidyl ether or the bis-glycidyl ether of bisphenol A may be mentioned as diepoxides which can be used according to the invention.

The proportions of catalysts used are generally 0.05 to 5% by weight, relative to the reaction mixture.

The epihalogenohydrin and the epoxides corresponding to the formula (V) are introduced as a mixture. Thus, the distribution of the units of the formula $CH_2X$ and of the groups of the formula (IV) in the products corresponding to the formula (III), and consequently that of the resulting units A and (II) in the products of the formula (I) according to the invention, is completely random. The relative proportion of the group of the formula A and of the group of the formula (II) is that of the epoxides used, that is to say $$\frac{n-p}{p}.$$

The preparation of the epoxides corresponding to the formula (V) and the intermediates corresponding to the formula (III) result from reactions of compounds having an alcohol group with epoxides; consequently, there are two possible structures for the various units, according to the two directions of opening of the epoxide group.

Thus, for the compounds corresponding to the formula (V), the configuration of the unit in brackets represents isomeric structures:

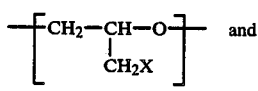  and  (Va)

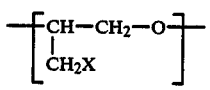  (Vb)

and the same applies to the compounds corresponding to the formula (III) as regards the group [C$_2$H$_3$(Y)—O], which represents:

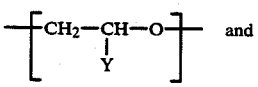  and  (IIIa)

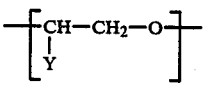  (IIIb)

and, in the formula (I), to $\{C_2H_3(Z)O\}$, which represents the following two structures:

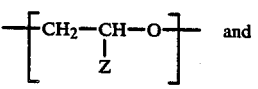  and  (Ia)

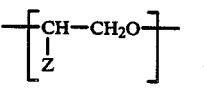  (Ib)

Nevertheless, for the products according to the invention, the isomers represented by the formulae (Va), (IIIa) and (Ia) are predominant.

The products corresponding to the formula (III) are subsequently converted to products of the formula (I) according to the invention, under various conditions, depending on the nature of the group A and Z, if appropriate after the volatile compounds have been removed by molecular distillation.

(a) When A denotes —CH$_2$OH, the replacement of the halogen atoms in the compounds of the formula (III) by hydroxyl groups can be carried out by reaction with an alkali metal salt of a carboxylic acid, and preferably with sodium acetate or potassium acetate, at a temperature of, say, 150° to 200° C., in a suitable solvent advantageously a glycol or glycol derivative; the acetic acid ester formed is then saponified by means of, say, sodium hydroxide or potassium hydroxide or alcoholysed by means of a lower alcohol such as methanol or ethanol, in the presence of a basic catalyst preferably sodium methylate or ethylate or potassium methylate or ethylate. This process is described in greater detail in U.S. Pat. No. 3,518,719.

(b) When A denotes the groups:

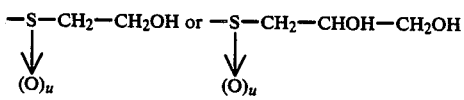

the replacement of the halogen atoms of the halogenopropoxy unit by thiohydroxyethyl groups corresponding to the formula:

—S—CH$_2$—CH$_2$OH or thiodihydroxypropyl groups:

—S—CH$_2$—CHOH—CH$_2$OH can be carried out by heating the intermediate of the formula (III) with 2-mercaptoethanol or 3-mercaptoglycerol, at a temperature of, say, 20° to 150° C., in the presence of an alkali metal compound, advantageously the hydroxide, methylate or ethylate of sodium or potassium, and preferably in the presence of a solvent such as an alcohol, glycol ether or polyglycol and, if appropriate, water.

The halogen substitution reaction can then be followed, if appropriate, by an oxidation reaction preferably carried out with hydrogen peroxide at a temperature of, say, 0° to 50° C. and preferably 30° to 40° C., in roughly stoichiometric proportions and advantageously in the presence of acetic acid. This process is described in greater detail in U.S. Pat. No. 3,906,048.

(c) When A denotes:

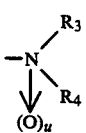

the compounds of the formula (I) can be obtained by heating the intermediate halogen compounds corresponding to the formula (III) with a secondary amine corresponding to the formula:

in which R$_3$ and R$_4$ have the same meaning as that indicated above, if appropriate in the presence of a solvent, particularly a glycol or alkoxyethanol, at atmospheric pressure or in an autoclave, at a temperature of, say, 50° to 160° C. The products are then oxidised, if appropriate, with hydrogen peroxide or a per-acid such as peracetic or performic acid, at temperatures of, say, 10° to 100° C.

(d) The compounds corresponding to the formula (I) in which A denotes a group corresponding to the formula:

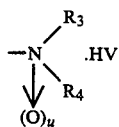

can be obtained by salifying the above compounds with a mineral or organic acid, preferably hydrochloric, hydrobromic, sulphuric, phosphoric, acetic, lactic, citric or tartaric acid, if appropriate in the presence of a solvent, especially an alcohol having, more particularly, 1 to 4 carbon atoms, to ensure the homogeneity of the reaction medium. (e) The compounds corresponding to the formula (I) according to the invention in which A denotes:

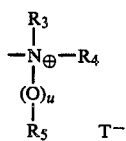

can be obtained from the compounds corresponding to the formula (I) in which A, forming part of Z, denotes the group corresponding to the formula (c), by alkylation with a compound of the formula $R_5T$, in which T and $R_5$ have the meanings indicated above, this compound preferably being methyl or ethyl chloride, bromide, iodide, sulphate, mesylate or tosylate or glycol chlorohydrin.

The alkylation reactions can be carried out with or without a solvent, typically an alcohol, or ether-alcohol, if appropriate in the presence of water, a chlorinated solvent or an aromatic solvent, at temperatures of, say, 10° to 80° C.

(f) The compounds corresponding to the formula (I) according to the invention in which A represents a group of the formula:

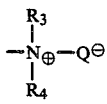

can be obtained from the compounds in which A denotes:

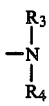

by alkylation with methyl or ethyl chloroacetate or chloropripionate, followed by saponification either with sodium chloroacetate or chloropropionate or potassium chloroacetate or chloropropionate, or alternatively with propane-sultone if $Q^-$ denotes the propyl-sulphonate anion.

(g) The compounds corresponding to the formula (I) in which A denotes the group $—OSO_3M$ can be obtained by sulphation of the compounds of the formula (I) in which A denotes the group $—CH_2OH$, with chlorosulphonic acid, if appropriate in the presence of a solvent, preferably chloroform, dichloroethane, benzene or toluene. If M denotes an alkali metal or one equivalent of an alkaline earth metal, the acid obtained is neutralised with the corresponding base.

(h) The compounds of the formula (I) in which A denotes the group

can be obtained by esterification of a compound corresponding to the formula (I) in which A denotes the group $—CH_2OH$, with sulphoacetic acid, the acid formed being neutralised, if appropriate, with an alkali metal base or alkaline earth metal base.

(i) The compounds of the formula (I) in which A denotes the group

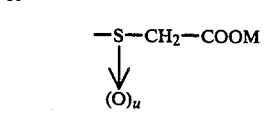

can be obtained by reacting the intermediate halogen compounds of the formula (III) with methyl or ethyl thioglycolate in the presence of sodium methylate or potassium methylate and an alcohol having 1 to 4 carbon atoms, acting as a solvent, at a temperature of, say, 80° to 120° C., this being followed, if u denotes 1, by oxidation with hydrogen peroxide or a per-acid.

The resulting ester is saponified and acidified to obtain the corresponding acid. The alkali metal salt can be obtained by neutralising the acid with corresponding base.

The mixtures of compounds of the formula (I) according to the present invention are generally in the form of viscous oils or pastes which are soluble or dispersible in water. These compounds usually have a molecular weight of 500 to 5,000.

We have discovered that these compounds can be used in various industries as surface-active agents, especially as low-foaming agents, as as wetting agents, detergents, peptising agents, dispersants, binders and anti-caking agents, as solubilising agents, penetrating agents, anti-redeposition agents and flotation agents, as antistatic finishes and as dyeing assistants.

The compositions of the present invention generally contain at least 0.2% by weight of a mixture of compounds corresponding to the formula (I). The proportion of the mixture of compounds of the formula (I) in the compositions can range up to, say, 80% by weight.

The compositions are generally aqueous or aqueous-alcoholic compositions, the alcohols being lower alcohols or alcohols based on glycol ethers.

We have noted more particularly that the compounds corresponding to the formula (I) possess a low aggressiveness towards the skin and the mucous membranes and that their properties are particularly valuable when they are used in cosmetic compositions or pharmaceutical compositions.

The invention thus also provides pharmaceutical or cosmetic compositions which are essentially characterised in that they contain at least one mixture of surface-active oligomers of this invention. The cosmetic compositions can include, in particular, compositions for the care of the skin, nails or hair.

In general, the cosmetic or pharmaceutical compositions according to the invention can be presented in various forms, such as in the form of aqueous, alcoholic or aqueous-alcoholic solutions, in the form of a cream, gel or emulsion or in the form of which it is packaged in an aerosol.

They usually contain the mixture of compounds corresponding to the formula (I) in amounts of 0.2 to 80% by weight, and advantageously 0.5 to 50%. by weight, relative to the total weight of the composition. The mixture of compounds of the formula (I) can be used, in particular, as the only surface-active agents or in a mixture with other surface-active compounds of the anionic, cationic, non-ionic or amphoteric type.

The compositions can also contain alkalising or acidifying agents, foam synergistic agents, foam stabilisers, thickeners, opacifiers, sequestering agents, superfatting agents, antiseptics, preservatives, anionic, cationic, non-ionic or amphoteric polymers or mixtures thereof, pigments, perfumes, dyestuffs, agents for imparting pearlescence, solvents, sun filters, oxidising agents, reducing agents, electrolytes, oils, waxes, natural substances, protein derivatives, antiserborrheic agents, anti-dyestuff agents and also may other active substance which can have an action in the treatment, care or protection of the skin or hair, and any adjuvants normally used in cosmetic compositions.

Acids and bases can be used in amounts appropriate for adjusting the pH of the compositions to, say, 3 to 12 and preferably 3 to 10.

Apart from the active substances for the treatment of the human or animal body and the oligomers according to the invention, the pharmaceutical compositions can contain pharmaceutically acceptable excipients.

For hair care, the compositions containing the compounds according to the invention can be, for example, shampoos, hair-conditioning compositions or dyeing compositions.

In addition to the mixture of random surface-active oligomers according to the invention, the shampoos can contain one or more anionic, cationic, amphoteric or non-ionic surface-active agents or a mixture thereof, and also other cosmetic adjuvants normally used in this type of composition.

The dyeing compositions can be based on so-called oxidation dyestuff precursors or so-called direct dyestuffs or mixtures thereof.

Depending on the nature of the components, the compositions according to the invention can also be used as lotions for rinsing the hair, fluid milks for the body, moisturising creams, lipsticks, eye shadows, wavesetting lotions and lacquers, and also for other cosmetic applications, these compositions always containing at least the surface-active random oligomers according to the invention.

The following Examples further illustrate the present invention.

EXAMPLE 1

Preparation of a mixture of compounds of the general formula (I) in which $R_1$ denotes $C_{12}H_{25}$, $\bar{n}=10$ and Z denotes, in the proportions $$\frac{n-p}{p} = \frac{7}{3},$$

$CH_2OH$ and the group of the formula II in which: $R_2$ denotes $C_{12}H_{25}$, $A=CH_2OH$ and $\bar{m}=0.5$.

(a) Preparation of the epoxide compounds of the formula V in which $R_2$ and $\bar{m}$ have the meaning indicated above and X denotes Cl.

1.2 ml of $BF_3$ etherate are added to 278 g (1.5 mols) of dodecan-1-ol sold under the trade name Alfol 12, and 208 g (2.25 mols) of epichlorohydrin are then added, at 50° C., in the course of 1 hour 15 minutes.

The temperature and the stirring are maintained for a further 15 minutes. A slightly yellow, viscous liquid with an epoxide number of zero is thus obtained.

475 g of t-butanol are added and 265 g of 40% strength sodium hydroxide solution are then added, at 50° C., in the course of 20 minutes, under a nitrogen atmosphere. After the mixture has been stirred for 1 hour at 50°–60° C., it is washed with 900 ml of hot water and then a further twice with 500 ml.

After the solvents have been evaporated off under reduced pressure, a virtually colourless liquid with an epoxide number of 3.3 milliequivalents/g and an organic chlorine number of 1.9 milliequivalents/g is obtained.

(b) Preparation of the mixture of intermediates of the formula III in which $R_1$, $\bar{n}$, $R_2$, $\bar{m}$ and X have the meanings indicated above.

0.25 ml of $BF_3$ etherate is added to 18.6 g (0.1 mol) of Alfol 12, and a mixture of 64.7 g (0.7 mol) of epichlorohydrin and 90.5 g (0.3 equivalent of epoxide) of compounds obtained in Example 1(a) above is then added, at 60° C., in the course of 1 hour 45 minutes. During the addition of the mixture of epoxide compounds, 0.52 ml of $BF_3$ is added in portions.

The temperature and the stirring are maintained for 30 minutes after the addition has ended.

The epoxide number of the reaction mixture is virtually zero.

(c) Preparation of the compounds of the formula I defined above.

170 g of diethylene glycol butyl ether (B.D.G.) and 86.2 g of potassium acetate are added to 172 g (0.86 equivalent of chlorine) of product obtained above, and the mixture is heated at 180° C. for 6 hours. The extent of reaction, measured by determining the chloride ions, is about 98%.

95 g of 40% strength sodium hydroxide solution and 100 ml of water are then added in the course of 45 minutes and the mixture is subsequently stirred at 40°–50° C. for 30 minutes to 1 hour. The reaction mixture is then neutralised with hydrochloric acid.

The organic phase is then separated off by decantation and the solvents are subsequently removed by heating under reduced pressure.

After the inorganic salts have been filtered off, a deep brown oil is obtained which is dispersible in water and soluble in vaseline oil.

The cloud point, measured at a concentration of 5% in butyldiglycol (B.D.G.) containing 25% of water, is 44° C.

EXAMPLE 2

Preparation of a mixture of compounds of the general formula I in which $R_1$ denotes a mixture of $C_8H_{17}$ and $C_{10}H_{21}$ radicals, $\bar{n}=9$ and Z denotes, in the proportions $$\frac{n-p}{p} = \frac{9-3}{3} = 2/1,$$

the group $CH_2OH$ and the group of the formula II in which: $R_2$ denotes $C_8H_{17}$ and $C_{10}H_{21}$, $A=CH_2OH$ and $\overline{m}=0.5$.

(a) Preparation of the epoxide compounds of the formula V in which $R_2$ and $\overline{m}$ have the meaning indicated above and X denotes Cl.

1 ml of $BF_3$ etherate is added to 215 g (1.5 mols) of Alfols 8/10, and 208 g (2.25 mols) of epichlorohydrin are then added, at 50° C., in the course of 1 hour 30 minutes.

The product obtained is taken up with 210 g of t-butanol, and 225 g of 40% strength sodium hydroxide solution are then added in the course of 30 minutes at 50°–60° C. After stirring for 1 hour, the reaction mixture is washed 3 times with respectively 600, 400 and 400 ml of hot water.

After drying, 360 g of a product are obtained in the form of a virtually colourless liquid.

$N_{epoxide}$: 3.9 milliequivalents/g
$N_{Cl}$: 2.0 milliequivalents/g (b) Preparation of the mixture of intermediates of the formula III in which $R_1$, $\overline{n}$, $R_2$, $\overline{m}$ and X have the meanings indicated above.

0.37 ml of $BF_3$ etherate is added to 14.3 g (0.1 mol) of Alfols 8/10, and 77 g (0.3 equivalent of epoxide group) of compounds obtained in the above example and 55.5 g (0.6 mol) of epichlorohydrin are then added, at 50° C., in the course of 1 hour 30 minutes.

(During the addition of the epoxide, a further 0.15 ml of $BF_3$ is added.) After stirring for a further 1 hour at 50° C., the epoxide number is virtually zero.

(c) Preparation of the compounds of the formula I defined above.

144.5 g of product obtained in this way are dissolved in 145 g of B.D.G. and, after the addition of 76 g (0.77 mol) of potassium acetate, the solution is then heated for 5 hours 30 minutes at 180° C.

It is left to cool to 50° C. and 152 g of 20% strength sodium hydroxide solution are then added in the course of 30 minutes.

After stirring for 1 hour 30 minutes, the mixture is diluted with 150 ml of hot water, any alkalinity is neutalised with hydrochloric acid, and the organic phase is decanted and then dried by heating under reduced pressure.

After the residual inorganic salts have been filtered off at 80° C., a thick water-dispersible oil having a cloud point in B.D.G. of 51° C. is obtained.

EXAMPLE 3

Preparation of a mixture of compounds of the general formula I in which $R_1$ denotes a mixture of $C_{16}H_{33}$ and $C_{18}H_{37}$ radicals, $\overline{n}=5$ and Z denotes the group of the formula II in which: $R_2$ denotes

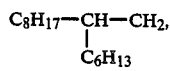

$A=CH_2OH$ and $\overline{m}=3$.

(a) Preparation of the compounds of the formula V in which $R_2$ and $\overline{m}$ have the above meaning and X denotes Cl.

0.76 ml of $BF_3$ etherate is added to 121 g (0.5 mol) of 2-hexyldecanol, and 185 g (2 mols) of epichlorohydrin are then added, at 50° C., in the course of 1 hour 30 minutes.

After stirring for a further 1 hour, 155 g of t-butyl alcohol are added and 75 g of 40% strength NaOH solution are then added at 50° C.

The stirring and heating are maintained for 1 hour. The organic phase is then washed 3 times with 400 ml of hot water and dried by heating under reduced pressure.

260 g of a product with an epoxide number of 1.53 milliequivalents/g and a chlorine number of 5.3 milliequivalents/g are thus obtained.

(b) Preparation of the mixture of intermediates of the formula III in which $R_1$, $\overline{n}$, $R_2$, $\overline{m}$ and X have the meaning indicated above.

0.22 ml of $BF_3$ is added to 6.5 g (0.025 mol) of a mixture of hexadecanol and octadecanol with a hydroxyl number of 3.8 milliequivalents/g, and 81.7 g (0.125 equivalent of epoxide groups) of compound obtained in Example 3(a) above are then added in the course of 1 hour 30 minutes at 50° C.

After stirring for 1 hour at 50° C., the reaction is virtually complete.

(c) Preparation of the compounds of the formula I indicated above.

The product obtained above is taken up in 90 g of dipropylene glycol. 43.5 g of potassium acetate are then added and the mixture is heated under a nitrogen atmosphere for 5 hours 30 minutes at 180° C.

The inorganic salts are filtered off and the solvent is distilled under reduced pressure.

The residual mixture is solubilised in 80 g of absolute ethanol and then, after the addition of 0.7 g of sodium methylate containing 5.8 milliequivalents/g, the mixture is left to stand overnight at ambient temperature.

The product obtained after distillation of the solvent is in the form of a thick brown oil which is sparingly soluble in water and soluble in vaseline oil.

EXAMPLE 4

Preparation of a mixture of compounds of the general formula I in which $R_1$ denotes a mixture of branched $C_{14}$, $C_{16}$ and $C_{18}$ alkyl radicals, $\overline{n}=4$ and Z denotes the group of the formula II in which: $R_2=C_{12}H_{25}$, $A=CH_2OH$ and $\overline{m}=2$.

(a) Preparation of epoxide compounds of the formula V in which $R_2$ and $\overline{m}$ have the above meaning and X denotes Cl.

1.15 ml of $BF_3$ etherate are added to 186 g (1 mol) of dodecan-1-ol, and 277.5 g (3 mols) of epichlorohydrin are then added, at 50° C., in the course of 1 hour 30 minutes.

After stirring for 1 hour, 230 g of t-butyl alcohol are added and 150 g of 40% strength sodium hydroxide solution are then added in the course of 20 minutes.

The stirring and heating are maintained for 1 hour and the reaction mixture is then washed 3 times with 500 ml of hot water.

The product obtained after heating under reduced pressure is in the form of a viscous liquid with an epoxide number of 2.2 milliequivalents/g and a chlorine number of 4.9 milliequivalents/g.

(b) Preparation of the mixture of intermediates of the formula II in which $R_1$, $\overline{n}$, $R_2$, $\overline{m}$ and X have the meanings indicated above.

0.2 ml of $BF_3$ etherate is added to 10 g (0.037 mol) of a mixture of branched $C_{14}$, $C_{16}$ and $C_{18}$ alcohols sold under the trade name Sidopol by Sidobre Sinnova and having a hydroxyl number of 3.7 milliequivalents/g, and 68.5 g (0.15 equivalent of epoxide groups) of the product obtained in accordance with Example 4(a) above are then added, at 50° C., in the course of 1 hour 30 minutes.

(c) Preparation of the compound of the formula I indicated above.

After heating for a further 1 hour, the reaction mixture obtained in step (b) of Example 4 is taken up with 80 g of dipropylene glycol, in the presence of 35 g of potassium acetate, and the mixture is heated for 5 hours 30 minutes at 180° C.

The inorganic salts are filtered off and the solvent is removed by heating under reduced pressure.

The residue is solubilised in 75 g of absolute ethanol and the solution is left to stand overnight at ambient temperature, in the presence of 0.6 g of sodium methylate. After the solvent has been evaporated off, a product is obtained in the form of a thick brown oil which is sparingly soluble in water and soluble in vaseline oil.

EXAMPLE 5

Preparation of a mixture of compounds of the general formula I in which $R_1$ denotes a mixture of $C_8H_{17}$ and $C_{10}H_{21}$ radicals, $\bar{n}=9$ and Z denotes, in the proportions $$\frac{n-p}{p} = \frac{9-3}{3} = 2/1,$$

the group $CH_2-OSO_3Na$ and the group of the formula II in which: $R_2=C_8H_{17}$ and $C_{10}H_{21}$, $A=CH_2-OSO_3Na$ and $\bar{m}=0.5$.

20 ml of chloroform are added to 23 g (0.5 equivalent of hydroxyl groups) of compounds obtained in accordance with Example 2(c), and 17.5 g (0.15 mol) of chlorosulphonic acid are then added dropwise, at 15°–17° C., under a stream of dry nitrogen, in the course of 30 minutes.

The reaction medium thickens during the addition.

It is diluted by adding 10 ml of chloroform.

The mixture is heated progressively to 60° C. and the solvent and the hydrochloric acid formed are then removed under reduced pressure.

After neutralisation with sodium hydroxide in the presence of isopropanol, and after the inorganic salts have been filtered off, the solvent is removed by heating under reduced pressure. A water-soluble brown paste is thus obtained.

EXAMPLE 6

Preparation of a mixture of compounds of the general formula I in which $R_1$ denotes radicals of lanolin alcohols, $\bar{n}=14$ and Z denotes, in the proportions $$\frac{n-p}{p} = \frac{14-2}{2} = 6/1,$$

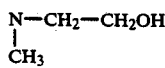

and the group of the formula II in which $R_2$=radicals of lanolin alcohols,

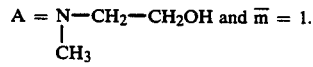

(a) Preparation of the epoxide compounds of the formula V in which $R_2$ and $\bar{m}$ have the meanings indicated above and X denotes Cl.

1.7 ml of $BF_3$ etherate are added to 300 g (0.72 equivalent of hydroxyl groups) of lanolin alcohols sold under the name Satulan, and 133 g (1.44 mols) of epichlorohydrin are then added dropwise, at 55° C., in the course of 1 hour 30 minutes. After stirring for 1 hour, the reaction mixture is taken up with 300 g of t-butanol, and 100 g of 40% strength sodium hydroxide solution are then added in the course of 30 minutes. After stirring for 30 minutes at 50°–60° C., the organic phase is washed with twice 800 ml of water at 70° C. After distillation under reduced pressure, a light yellow paste with an epoxide number of 2.0 milliequivalents/g is obtained.

(b) Preparation of the mixture of intermediates of the formula III in which $R_1$, $\bar{n}$, $R_2$, $\bar{m}$ and X have the meanings indicated above.

0.63 ml of $BF_3$ etherate is added to 40.6 g (0.1 equivalent of hydroxyl groups) of Satulan, and a mixture of 100 g (0.2 equivalent of epoxide groups) of compounds obtained in accordance with Example 6(a) above and 111 g (1.2 mols) of epichlorohydrin is then added at 70° C. The addition lasts 3 hours. During the addition, 0.63 ml and 0.25 ml of $BF_3$ are added.

The temperature is maintained for a further 1 hour after the addition has ended.

After cooling, a paste with glints of fluorescent green is obtained.

(c) Preparation of the compounds of the formula I indicated above.

50 g (0.66 mol) of N-methylethanolamine are added to 50 g (0.27 equivalent of chlorine) of product obtained in accordance with Example 6(b) above, and the mixture is then heated for 3 hours, at 140° C., under a nitrogen atmosphere.

The reaction mixture is washed 3 times with 100 ml of water at 90° C., in the presence of 20 ml of n-butanol for the first decantation. After drying under reduced pressure, a light brown paste which is soluble in water above 56° C. is obtained. Base number: 3.5 milliequivalents/g.

EXAMPLE 7

Preparation of a mixture of compounds of the general formula I in which $R_1$ denotes radicals of lanolin alcohols, $\bar{n}=14$ and Z denotes, in the proportions $$\frac{n-p}{p} = 6/1,$$

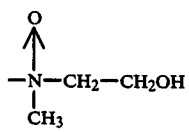

and the group II in which: $R_2$=radicals of lanolin alcohols,

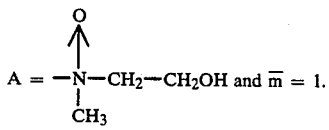

$$A = -\underset{\underset{CH_3}{|}}{N}-CH_2-CH_2OH \text{ and } \overline{m} = 1.$$

25 ml of water and 6 ml of hydrogen peroxide of 130 volumes strength are added, at 40°–50° C., in the course of 1 hour, to 20 g (0.7 basic equivalent) of compounds obtained in accordance with Example 6(b).

The concentrations of the solution is adjusted to 35% and the solution is then left to stand for 48 hours at ambient temperature.

The thick light yellow solution thus obtained is soluble in water with a very slight opalescence.

EXAMPLE 8

Preparation of a mixture of compounds of the general formula I in which $R_1$ denotes radicals of lanolin alcohols, $\overline{n}=14$ and Z denotes, in the proportions 6/1,

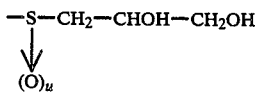

$$-S-CH_2-CHOH-CH_2OH$$
$$\downarrow$$
$$(O)_u$$

and the group of the formula II in which: $R_2$ denotes radicals of lanolin alcohols,

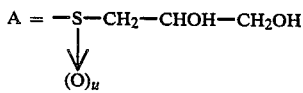

$$A = -S-CH_2-CHOH-CH_2OH$$
$$\downarrow$$
$$(O)_u$$

and $\overline{m}=1$.

(a) Preparation of the mixture of compounds of the formula I defined above, in which $u=0$.

100 g of methoxyethanol and 32.3 g (0.27 equivalent) of thioglycerol are added to 50 g (0.27 equivalent of chlorine) of compounds obtained in accordance with Example 6(b). The mixture is heated at 60° C. under a nitrogen atmosphere and 27 g of 40% strength sodium hydroxide solution are added dropwise in the course of 45 minutes. After the addition, the mixture is heated for a further 2 hours 30 minutes at 90° C. The water is removed by distillation and the sodium chloride is filtered off. The filtrate is then evaporated to dryness.

A water-soluble light chestnut paste is thus obtained. Thioether number: 3.4 milliequivalents/g.

(b) Preparation of the mixture of compounds of the formula I defined above, in which $u=1$.

36 g of product obtained in accordance with Example 8(a) above are dissolved in 100 ml of water. 0.6 g of acetic acid is added and 6.9 ml of hydrogen peroxide of 200 volumes strength are then added dropwise at 35° C.

A slightly opalescent, light brown solution is obtained.

EXAMPLE 9

Preparation of a mixture of compounds of the general formula I in which $R_1$ denotes radicals of lanolin alcohols, $\overline{n}=14$ and Z denotes, in the proportions 6/1, $SCH_2COONa$ and the group of the formula II in which: $R_2$ denotes radicals of lanolin alcohols, $A=-S-CH_2-COONa$ and $\overline{m}=1$.

100 g of methoxyethanol and 32.6 g (0.27 mol) of ethyl thioglycolate are added to 50 g (0.27 equivalent of chlorine) of compounds obtained in accordance with Example 6(b), and 46 g of sodium methylate in methanol (0.27 equivalent) are then added, at 60° C., under nitrogen.

After heating for 1 hour at 60° C., the mixture is heated progressively to 95° C., the methanol being removed, and this temperature is maintained for 2 hours.

The sodium chloride is filtered off and the ester groups are saponified by adding 27 g of 40% strength sodium hydroxide solution.

After distillation of the solvents, a water-soluble brown paste is obtained.

EXAMPLE 10

The following dyeing composition is prepared:

| | |
|---|---|
| Oxyethyleneated nonylphenol containing 4 mols of ethylene oxide (EO)(per mole of phenol) | 22 g |
| Oxyethyleneated nonylphenol containing 9 mols of ethylene oxide | 22 g |
| Propylene glycol | 10 g |
| Ethyl alcohol | 8 g |
| Compounds of Example 9 | 2 g |
| Sodium salt of diethylenetriaminepenta-acetic acid | 2.4 g |
| 35° Be strength sodium bisulphite solution | 1.3 g |
| 22° Be strength ammonia solution | 10.2 g |
| Hydroquinone | 0.15 g |
| Para-aminophenol | 0.1 g |
| Para-phenylenediamine | 0.1 g |
| Meta-aminophenol | 0.05 g |
| Resorcinol | 0.15 g |
| Distilled water q.s.p. | 100 g |

This composition, diluted with an equal weight of hydrogen peroxide of 20 volumes strength, gives a gel which is applied to a deep blond head of hair for 30 minutes. After rinsing, shampooing and drying, a pearlescent light blond coloration is obtained.

EXAMPLE 11

The following dyeing composition is prepared:

| | |
|---|---|
| Lauryl diethanolamide | 5 g |
| Sodium salt of sulphated oxyethyleneated lauryl alcohol, containing 30% of active ingredient | 20 g |
| Compounds of Example 6 | 5 g |
| Hydroxyethylcellulose | 1 g |
| 2-Ethoxyethanol | 10 g |
| 2-[N—(β-hydroxyethyl)-amino]-5-hydroxy-nitrobenzene | 0.4 g |
| 3-[N—(β-hydroxyethyl)-amino]-4-[N—(β-hydroxyethyl)-amino]-nitrobenzene | 0.15 g |
| Citric acid q.s.p. | pH 9 |
| Distilled water q.s.p. | 100 g |

This composition is in the form of a slightly thickened liquid which is applied to a deep blond head of hair for 20 minutes. After rinsing and drying, the hair possesses a coppery red sheen.

EXAMPLE 12

The following composition is prepared:

| | |
|---|---|
| Compounds of Example 2 | 0.7 g |
| Sodium salt of sulphated alkanol ($C_{12}$–$C_{14}$) oxyethyleneated with 2.2 mols of ethylene oxide, containing 25% of active ingredient | 40.0 g |

-continued

| | |
|---|---|
| Cycloimidazoline derivative of coconut oil, sold by MIRANOL under the name MIRANOL C 2 M CONC | 25.0 g |

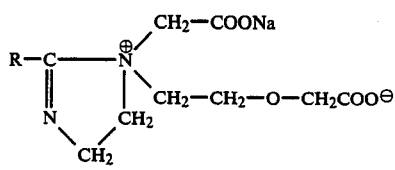

R = copra,
as a solution containing 40% of active ingredient

| | |
|---|---|
| Copra diethanolamide | 2.0 g |
| Hydrochloric acid q.s. | pH 7.4 |
| Water, dyestuff, preservative, perfume q.s.p. | 100 g |

This composition is used as a shampoo.

EXAMPLE 13

The following composition is prepared:

| | |
|---|---|
| Compounds of Example 9 | 0.5 g |
| Glucoside alkyl ether sold under the name TRITON CG 110 by SEPPIC as a solution containing 30% of active ingredient | 24.0 g |
| Surface-active agent of the formula: $R-CHOH-CH_2OH(CH_2-CHOH-CH_2-O)_nH$ R = mixtures of $C_9-C_{12}$ alkyl radicals and n = 3.5 (statistical average value) | 5.0 g |
| Polysorbate 20 [polyoxyethylene (20) sorbitan monolaurate] sold by ATLAS under the name TWEEN 20 | 2.0 g |
| Sodium hydroxide q.s. | pH 6 |
| Water, dyestuff, preservative, perfume, q.s.p. | 100 g |

This composition is used as a shampoo.

EXAMPLE 14

The following composition is prepared:

| | |
|---|---|
| Compounds of Example 6 | 1.0 g |
| Triethanolamine alkyl($C_{12}-C_{14}$)-sulphate containing 40% of active ingredient | 25.0 g |
| $C_{12}-C_{14}$ alcohol oxyethyleneated with 10 mols of ethylene oxide and carboxymethylated, sold under the name AKYPO RLM 100 by Chem'Y (active ingredient) | 4.5 g |
| Sodium hydroxide q.s. | pH 8.6 |
| Water, dyestuff, preservative, perfume, q.s.p. | 100 g |

This composition is used as a shampoo.

EXAMPLE 15

The following composition is prepared:

| | |
|---|---|
| Compounds of Example 2 | 1.9 g |
| Mixture of cetyl/stearyl alcohol and oxyethyleneated cetyl/stearyl alcohol containing 15 mols of ethylene oxide | 3.0 g |
| Hydroxyethylcellulose sold under the name Cellosize QP 4400 H | 0.4 g |
| Distearyldimethylammonium chloride | 0.4 g |
| Sodium hydroxide q.s. | pH 6.7 |
| Water, dyestuff, preservative, perfume, q.s.p. | 100 g |

This composition is used as a lotion for rinsing the hair.

EXAMPLE 16

The following composition is prepared:

| FLUID MILK FOR THE BODY | |
|---|---|
| Compounds of Example 3 | 10 g |
| Isopropyl myristate | 40 g |
| Preservative | qs |
| Antioxidants | qs |
| Perfume | qs |
| Sterile demineralised water q.s.p. | 100 g |

EXAMPLE 17

The following composition is prepared:

| MOISTURISING CREAM | |
|---|---|
| Compounds of Example 3 | 5 g |
| Glycerol monostearate | 5 g |
| Amerchol L 101 | 5 g |
| Cetiol LC | 30 g |
| Sodium lactate | 3 g |
| Antioxidants | qs |
| Preservatives | qs |
| Perfume | qs |
| Sterile demineralised water q.s.p. | 100 g |

EXAMPLE 18

The following composition is prepared:

| LIPSTICK | |
|---|---|
| Compounds of Example 3 | 14 g |
| Indopol H 300 | 14 g |
| Stellanol M 32 | 15 g |
| Miglyol 810 | 19 g |
| Jojoba oil | 12 g |
| Argobase | 3.5 g |
| New Mekon White wax | 10 g |
| Syncrowax E.R.L.C. | 2.5 g |
| Antioxidants | qs |
| Dyestuff and pigments | qs |
| Perfume q.s. | 100 g |

EXAMPLE 19

The following composition is prepared:

| MOISTURISING CREAM | |
|---|---|
| Compounds of Example 4 | 5 g |
| Glycerol monostearate | 10 g |
| Sweet-almond oil | 30 g |
| Octyloxyglyceryl palmitate | 10 g |
| Antioxidants | qs |
| Preservatives | qs |
| Perfume | qs |
| Sterile demineralised water q.s.p. | 100 g |

EXAMPLE 20

The following composition is prepared:

| EYE SHADOW | |
|---|---|
| Talc | 23.65 g |
| Titanium oxide | 15 g |
| Manganese violet | 1.20 g |
| Black iron oxide | 0.3 g |
| Ferric blue | 0.8 g |
| Mica | 40 g |

EYE SHADOW

| | |
|---|---|
| Bismuth oxychloride | 4 g |
| Vaseline oil | 10 g |
| Isopropyl myristate | 1.5 g |
| Compounds of Example 4 | 1.9 g |
| Oleyl alcohol | 1.5 g |
| Calcium stearate | 0.1 g |
| B.H.A. | 0.05 g |

EXAMPLE 21

The following composition is prepared:

LIQUID REDUCER FOR PERMANENT WAVING

| | |
|---|---|
| Ammonium thioglycolate | 9.5 g |
| Ammonium thiolactate solution (50% strength) | 4.0 g |
| Ammonium solution (20% strength) | 2.0 g |
| Ammonium bicarbonate | 7.0 g |
| Sequestering agent | 0.2 g |
| Surface-active oligomers of Example 2 | 1.0 g |
| Oxyethyleneated fatty alcohol (20 EO) | 1.0 g |
| Perfume, opacifier, dyestuff, deionised water q.s.p. | 100 ml |

EXAMPLE 22

The following composition is prepared:

LIQUID REDUCER FOR PERMANENT WAVING

| | |
|---|---|
| Thioglycolic acid | 7.0 g |
| Ammonia solution (20% strength) | 6.5 g |
| Ammonium bicarbonate | 6.0 g |
| Sequestering agent | 0.2 g |
| Surface-active oligomers of Example 9 | 0.5 g |
| Oxyethyleneated fatty alcohol (20 EO) | 1.0 g |
| Perfume, opacifier, dyestuff, deionised water q.s.p. | 100 ml |

EXAMPLE 23

The following composition is prepared:

LIQUID OXIDISER OR FIXER FOR PERMANENT WAVING

| | |
|---|---|
| Hydrogen peroxide | 8 volumes strength |
| Stabilisers | 0.2 g |
| Surface-active oligomers of Example 6 | 0.5 g |
| Oxyethyleneated nonylphenol (9 EO) | 1.0 g |
| Perfume, opacifier, dyestuff, deionised water q.s.p. | 100 ml |

EXAMPLE 24

The following composition is prepared:

| | |
|---|---|
| Compounds of Example 6 | 0.2 g |
| PVP/VA E 735 | 1.5 g (active ingredient) |
| Ethyl alcohol q.s.p. | 50° strength |
| Water q.s.p. | 100 cc |

The composition is very slightly opalescent.

EXAMPLE 25

The following composition is prepared:

| | |
|---|---|
| Compounds of Example 9 | 0.3 g |
| PVP/VA E 735 | 1 g (active ingredient) |
| Ethyl alcohol q.s.p. | 10° strength |
| Water q.s.p. | 100 cc |

The composition is very slightly opalescent.

EXAMPLE 26

The following composition is prepared:

| | |
|---|---|
| Compounds of Example 6 | 0.2 g |
| PVP/VA E 735 | 1.5 g (active ingredient) |
| Gafquat 734 | 0.5 g (active ingredient) |
| Ethyl alcohol q.s.p. | 50° strength |
| Water q.s.p. | 100 cc |

The composition is very slightly opalescent.

The compositions of Examples 24, 25 and 26 are used as leave-on wavesetting lotions.

In these examples, PVP/VA E 735 denotes a vinylpyrrolidone/vinyl acetate (70/30) copolymer.

EXAMPLE 27

The following composition is prepared:

| | |
|---|---|
| Compounds of Example 2 | 0.2 g |
| PVP/VA E 335 | 2 g (active ingredient) |
| 96° strength ethyl alcohol q.s.p. | 100 g |

The composition is limpid. When it has been introduced into a spray bottle, it is used as a hair lacquer.

PVP/VA E 335 denotes a vinylpyrrolidone/vinyl acetate (30/70) copolymer.

The commercial names and trade marks of the products used in the Examples represent the following products:

AMERCHOL L 101 Extract of lanolin alcohols sold by AMERCHOL
CETIOL LC Cetyl laurate sold by HENKEL
INDIPOL H 300 Polyisobutylene sold by AMOCO
STELLANOL M 32 Lanolin alcohols sold by STELLA
MIGLYOL 810 Triglycerides of saturated fatty acid (C8 to C12) of vegetable origin sold by DYNAMIT NOBEL
ARGOBASE Lanolin derivatives sold by WEST BROOK LANOLIN COMPANY
NEW MEKON WHITE WAX Microcrystalline wax sold by RAFFINERIE FRANCAISE D'OSOKERITE
SYNCROWAX E R L C Distearyl ester of glycol sold by CRODA
GAFQUAT 734 Quaternary vinylpyrrolidone copolymer of molecular weight about 100,000 sold by GAF.

We claim:

1. A hair dye composition comprising in an aqueous, alcoholic or aqueous alcoholic medium an effective amount of a hair dye to dye said hair and surface-active random oligomer having the formula

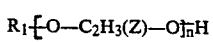

wherein
- $R_1$ represents a linear or branched, saturated or unsaturated aliphatic hydrocarbon radical, a cycloaliphatic radical, an aromatic radical or an alkyl aromatic radical, containing up to 30 carbon atoms,
- Z represents (i) a group having the formula, $R_2O\text{-}[C_2H_3(A)\text{--}O]_{\overline{m}}CH_2\text{--}$, or (ii) a mixture of (i) and A, wherein
- A represents a non-ionic, cationic, anionic, or zwitterionic group,
- $R_2$ represents a linear or branched, saturated or unsaturated aliphatic hydrocarbon radical, a cycloaliphatic radical, an aromatic radical or an alkyl aromatic radical, containing 8 to 30 carbon atoms,
- $\overline{n}$ represents an average statistical value ranging from 1 to 20, and
- $\overline{m}$ represents an average statistical value ranging from 0.5 to 10.

2. A hair dye composition comprising in an aqueous, alcoholic or aqueous alcoholic medium an effective amount of a hair dye to dye said hair and a surface-active random oligomer having the formula $$R_1\text{--}O\text{-}[C_2H_3(Z)\text{--}O]_{\overline{n}}H$$

wherein
- $R_1$ represents a linear or branched, saturated or unsaturated aliphatic hydrocarbon radical, a cycloaliphatic radical, an aromatic radical or an alkyl aromatic radical, containing up to 30 carbon atoms,
- Z represents (i) a group having the formula, $R_2O\text{-}[C_2H_3(A)\text{--}O]_{\overline{m}}CH_2\text{--}$, or (ii) a mixture of (i) and A, wherein
- A is selected form the group consisting of
  (a) —CH₂OH,

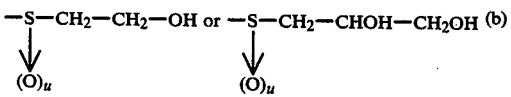  (b)

wherein u denotes 0 or 1,

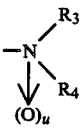  (c)

wherein $R_3$ and $R_4$ each independently represent alkyl or hydroxyalkyl containing 1–3 carbon atoms; or $R_3$ and $R_4$ together with the nitrogen atom to which they are attached form a heterocycle having 5 or 6 ring members, and u denotes 0 or 1,

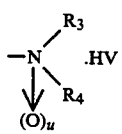  (d)

wherein HV denotes a mineral or organic acid, and u, $R_3$ and $R_4$ having the meanings given in (c) above,

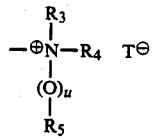  (e)

wherein $R_5$ represents methyl, ethyl or hydroxyethyl, $T^{\ominus}$ denotes an anion, and u, $R_3$ and $R_4$ have the meanings given in (c), above,

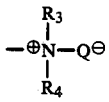  (f)

wherein $Q^{\ominus}$ represents $CH_2COO^-$, $CH_2CH_2COO^-$ or $(CH_2)_3SO_3^-$ and $R_3$ and $R_4$ have the meanings given in (c), above, (g) —OSO₃M wherein M denotes hydrogen or alkali metal or one equivalent of an alkaline earth metal, (h) —OCOCH₂SO₃M wherein M has the meaning given in (g), above, and

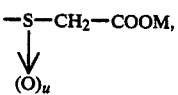  (i)

wherein M has the meaning given in (g), above, and u denotes 0 or 1,
- $R_2$ represents a linear or branched, saturated or unsaturated aliphatic hydrocarbon radical, a cycloaliphatic radical, an aromatic radical or an alkylaromatic radical, containing 8 to 30 carbon atoms,
- $\overline{n}$ represents an average statistical value ranging from 1 to 20, and
- $\overline{m}$ represents an average statistical value from 0.5 to 10.

3. The hair dye composition of claim 1 wherein said surface-active random oligomer is present in an amount ranging from 0.2 to 80 percent by weight of said compositions.

4. A hair dye composition comprising in an aqueous, alcoholic or aqueous alcoholic medium an effective amount of a hair dye to dye said hair and a surface-active random oligomer having the formula $$R_1\text{--}O\text{-}[C_2H_3(Z)\text{--}O]_{\overline{n}}H$$

wherein
- $R_1$ represents a mixture of $C_8H_{17}$ and $C_{10}H_{21}$,
- Z represents a mixture of (i) $CH_2OH$ and (ii) $R_2O\text{-}[C_2H_3(CH_2OH)\text{--}O]_{\overline{m}}CH_2\text{--}$ wherein the ratio of (i):(ii) is 2:1 and $R_2$ represents a mixture of $C_8H_{17}$ and $C_{10}H_{21}$,
- $\overline{n}$ represents an average statistical value of 9, and
- $\overline{m}$ represents an average statistical value of 0.5.

5. The hair dye composition of claim 4 wherein said surface-active random oligomer is present in an amount ranging from 0.2 to 80 percent by weight of said composition.

6. A hair dye composition comprising in an aqueous, alcoholic or aqueous alcoholic medium an effective amount of a hair dye to dye said hair and a surface-active random oligomer having the formula $R_1-O-[C_2H_3(Z)-O]_{\overline{m}}H$ wherein
- $R_1$ represents a linear or branched, saturated or unsaturated aliphatic hydrocarbon radical, a cycloaliphatic radical, an aromatic radical or an alkyl aromatic radical, containing up to 30 carbon atoms,
- Z represents (i) a group having the formula, $R_2O-[C_2H_3(A)-O]_{\overline{m}}CH_2-$, or (ii) a mixture of (i) and A, wherein A represents a non-ionic, cationic, anionic, or zwitterionic hydrophilic group,
- $R_2$ represents a linear or branched, saturated or unsaturated aliphatic hydrocarbon radical, a cycloaliphatic radical, an aromatic radical or an alkyl aromatic radical, containing 8 to 30 carbon atoms,
- $\overline{n}$ represents an average statistical value ranging from 1 to 20, and
- $\overline{m}$ represents an average statistical value ranging from 0.5 to 10.

* * * * *